United States Patent [19]

Okada et al.

[11] Patent Number: 4,754,264

[45] Date of Patent: Jun. 28, 1988

[54] WATER CONTENT DETECTING DEVICE FOR DIAPER

[75] Inventors: Shigeru Okada; Katsutoshi Rokuta; Toshio Ikegawa, all of Kochi, Japan

[73] Assignee: Nippon Kodoshi Corporation, Kochi, Japan

[21] Appl. No.: 867,501

[22] Filed: May 28, 1986

[30] Foreign Application Priority Data

Jun. 3, 1985 [JP] Japan .............................. 60-084351[U]
Feb. 27, 1986 [JP] Japan .............................. 61-028796[U]

[51] Int. Cl.$^4$ ............................................. G08B 21/00
[52] U.S. Cl. ................................ 340/573; 128/138 A; 340/604
[58] Field of Search ............................... 340/573, 604; 128/138 A; 324/61 P

[56] References Cited

U.S. PATENT DOCUMENTS 3,460,123 8/1969 Bass ....................................... 340/573
3,824,460 7/1974 Gustafson ............................ 340/604
4,539,559 9/1985 Kelly et al. ........................... 340/573
4,653,491 3/1987 Okada ............................... 128/138 A

FOREIGN PATENT DOCUMENTS 2113438 8/1983 United Kingdom ............. 128/138 A

Primary Examiner—Glen R. Swann, III
Attorney, Agent, or Firm—Shlesinger Arkwright & Garvey

[57] ABSTRACT

A water content detecting device for any type of diaper such as a cloth made reusable diaper, a paper made disposable diaper, or the like includes a sensing unit for sensing the degree of wetness of the diaper and an informing unit for transmitting the information representing the degree of wetness to a nursing person at a remote place. The sensing unit is detachably interposed in the diaper to be detected. The sensing unit is composed of a water impermeable upper sheet, a water permeable lower sheet, and a pair of metal layers placed between the upper sheet and the lower sheet and extending in the longitudinal direction of the sheets in parallel. One of the metal layers is covered with an electrical insulating layer. The informing unit is connected to the sensing unit through a pair of leads, and composed of a water content detecting circuit for detecting the change of electrostatic capacitance between the two metal layers of the sensing unit, a wave form shaping circuit, and an oscillating circuit. This water content detecting circuit mainly consists of an astable multivibrator which uses the two metal layers of the sensing unit as its feedback capacitor.

5 Claims, 3 Drawing Sheets

WATER CONTENT DETECTING DEVICE FOR DIAPER

BACKGROUND OF THE INVENTION

1. Field of the Invention

The present invention generally relates to a water content detecting device for a diaper to encourage prompt changing of the same when wet. In its particular aspects, the present invention relates to a device containing a sensing unit for detecting the water content in any type of diaper such as a cloth-made diaper and a paper made disposable diaper and an informing unit for transmitting the information regarding the water content to a remote place.

2. Description of the Prior Art

Recently, the number of aged people has increased owing to the progress of medical science, and also the number of bed ridden people has tended to increace simultaneously. In nursing hospitals for such aged people, it is estimated that at least 30 percent of the patients are ridden. For nursing such patients, the treatment of excrements has been a serious problem. It is obvious that providing easy treatment for at least urine would lighten the distress and burden on the patients and nursing people. Conventionally, two manners have been commonly used for such urine treatment. One manner is a diaper treatment using a diaper or napkin to absorb the excreted urine. The other manner is a continuous urine excretion treatment system using an urethral catheter such as balloon catheter which must be always outfitted to the patient.

The above mentioned diaper treatment will be discussed in detail as the present invention is related to this treatment. In hospitals or nursing homes, the time for changing diapers of patients is fixed at specified intervals, since the nurse does not know the urination pattern of all the patients. However, with this manner, some of the patients may be left with a wet diaper for a long time causing discomfort and pain owing to a diaper rash, cooling, bed sores and the like.

In order to determine the urination pattern of such patients, a particular method to detect the water content in urine has been provided. The method for detecting the water content by means of change in electric conductivity of electrodes such as an electric wire installed in the diaper, has been applied. Further, a structure of a capacitor is formed in the diaper so that the degree of wetness can be determined by detecting the change in electrostatic capacity of the capacitor. These water content detecting methods have been proposed in our prior inventions (Japanese Patent Application for Utility Model No. 58-202267, No. 57-71558 and Japanese Patent Applications No. 59-128237, No. 59-128238 and No. 59-143649).

These methods can provide comfort to the patients since wet diapers can be changed by the nurse or nursing person informed of the wet condition of the diaper through electrical means. However, these methods require prior assembly of the electric wire or the metal layers to form the capacitor in the diaper. The patients may be inconvenienced since only such specially made diapers, particularly disposable diaper, are effective. Further, many aged people prefer to use a conventional cloth type diaper capable of reuse.

The electric wire type water content detecting diaper often causes troubles owing to breaking, disconnecting or twisting by the movement of the patients or babies or whoever is wearing this type diaper. Further this type of diaper can not detect the degree of wetness of the diaper without being checked directly by a nursing person.

On the other hand, the capacitor type water content detecting diaper can detect the degree of wetness of the diaper by measurement of the change of electrostatic capacitance. In the above described conventional invention, the electrostatic capacitance is measured by an AC bridge method referred in JIS (Japanese Industrial Standard) C-5102. This AC bridge method always requires an AC power source, so that this method consumes a relatively large amount of electrical energy. Additionally the change of electrostatic capacitance is detected by a coil having the value of inductance corresponding to the frequency of the AC power source. This makes the detecting circuit complicated, thereby increasing its manufacturing cost.

SUMMARY OF THE INVENTION

It is an object of the present invention to provide a water content detecting device which is available for any type of diaper such as a disposable paper diaper, a cloth type diaper capable of reusing and so on in addition to a specially made diaper previously assembled with the water content detecting device.

Another object of the present invention is to provide a water content detecting device for a diaper which can detect the degree of wetness of the diaper without being checked directly by a nursing person at a remote place.

A further object of the present invention is to provide a water content detecting device for a diaper which can be simply constructed inexpensively manufactured and require only a minimal amount of energy to operate.

To accomplish the above mentioned objects, the water content detecting device for a diaper according to the present invention comprises a sensing unit for the degree of wetness of a diaper and an informing unit for transmitting the information representing the degree of wetness to a remote place.

This sensing unit is composed of a water permeable upper sheet, a water impermeable lower sheet, and a pair of metal layers placed between the water permeable upper sheet and the water impermeable lower sheet and extending in the longitudinal direction of the sheets in parallel. The surface of one of the metal layers is covered with an electrical insulating layer. This sensing unit is detachably interposed in the diaper to be detected.

The informing unit is composed of a water content detecting circuit for detecting the change of electrostatic capacitance between the two metal layers of the sensing unit, a wave form shaping circuit, and an oscilating circuit. This water content detecting circuit is a multivibarator which uses the two metal layers of the sensing unit as its feedback capacitor.

According to the above mentioned composition, the two metal layers, which one of them is covered with an electric insulating layer, form a capacitor, and the electrostatic capacitance of this capacitor is varied by the water content between the layers. The degree of wetness of the diaper is determined by the level of the electrostatic capacitance. The detecting circuit is actuated when the electrostatic capacitance of the capacitor installed in the diaper has reached a predetermined. The detected signal from this detecting circuit is output from the oscillating circuit through the wave form shaping circuit. This oscillating signal is transmitted to a remote place, so that the nursing personnel at a remote place will know which diaper to change.

The sensing unit can be used for any type of diaper such as a reusable cloth diaper, an ordinary disposable paper, and so on. In detail, the sensing unit is inserted in the diaper and electrically connected to the informing unit. This sensing unit is separated from the informing unit and disposed as the diaper is changed.

The water content detecting circuit of the informing unit does not need an AC power source and a variable capacitor for tuning in order to measure the electrostatic capacitance in conventional manners. Thus a frequency converter for adjusting the frequency of the AC power source to a specific value and its operation are not required. This will reduce its initial cost (manufacturing cost) and running cost (energy consumption).

Other objects, features and advantages of the present invention will become apparent upon perusal of the following detailed description of the preferred embodiments of the present invention when taken in conjunction with the appended drawings.

DETAILED DESCRIPTION OF THE PREFERRED EMBODIMENT

Figure 1:
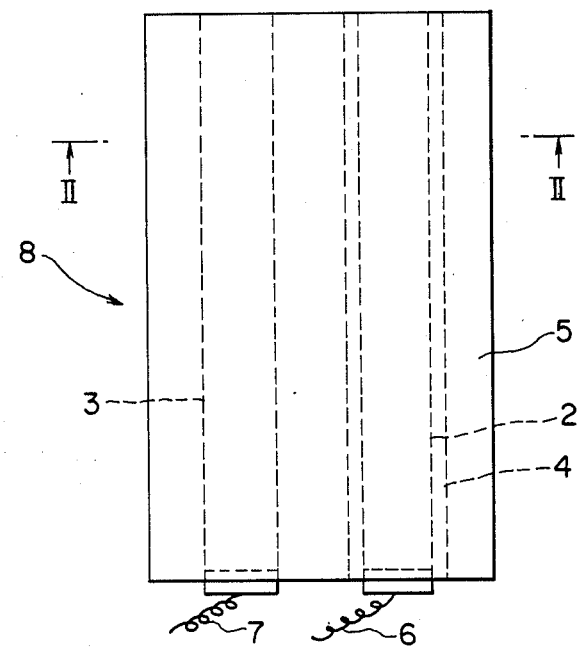
FIG. 1 is a plan view showing one embodiment of a sensing unit of the water content detecting device according to the present invention.
Figure 2:
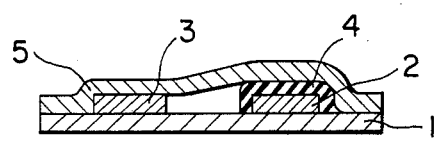
FIG. 2 is a sectional view taken along the line II—II in FIG. 1.

Referring to FIG. 1, there is shown the structure of one embodiment of the sensing unit for detecting the degree of wetness of a diaper. Also FIG. 2 shows the cross sectional view taken along the line II—II of FIG. 1. The sensing unit is composed of a water impermeable lower sheet 1, a pair of metal layers 2 and 3 formed on the lower sheet 1, an electric insulating layer 4 layered on one metal layer 2 so as to cover it, and a water permeable upper sheet 5.

The lower sheet 1 is a plastic film having its thickness of 3 to 30 $\mu$m such as a polyethylene, polypropylene, polyester, vinyl chloride or the like.

The metal layers 2 and 3 are formed in a thin layer on the lower sheet 1 by means of lamination or vacuum evaporation of metal material such as aluminium, zinc, copper, tin or the like. These metal layers are separated at a constant distance and extend in parallel to each other in the longitudinal direction of the lower sheet 1. Preferable dimension of the metal layers 2 and 3 are a width of 5 to 20 mm and a thickness of 15 micrometers or less. The distance between the metal layers 2 and 3 is preferably 2 to 20 mm.

The electric insulating layer 4 is formed in a thin layer having a thickness of 20 micrometers or less made of silicon resin, acryl resin, polyamide resin, polyimide resin, nitrile rubber, wax, sodium silicate, polyvinyl alchole, vinyl acetate or the like. Alternatively, the insulating layer 4 may be formed by a laminating treatment using a plastic film having a thickness of 2 to 20 $\mu$m such as polypropylene, polyethylene, polyester, polyamide or the like.

The water permeable upper sheet 5 is made of a paper having a thickness of 15 to 150 $\mu$m or a non-woven sheet with a texture rate of 120 g/m$^2$ or less such as rayon, polypropylene, polyester fiber, or the like. This water permeable upper sheet 5 is secured to the lower sheet 1 so as to cover the metal layers 2 and 3, and the lower sheet 1. The water permeable upper sheet 5 can absorb water and form a continuous water phase in it.

Figure 3:
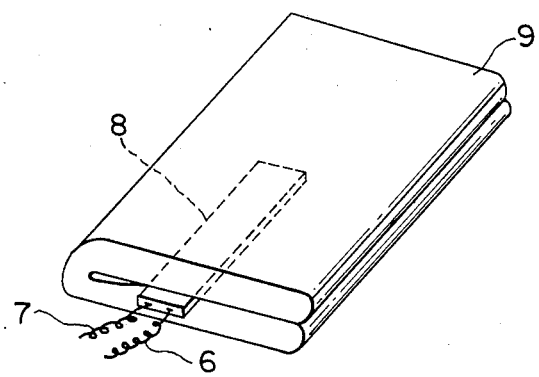
FIG. 3 is a schematic perspective view showing the sensing unit inserted in a diaper.

One end of metal layers 2 and 3 are pespectively connected to leads 6 and 7 that are subsequently connected to a water content detecting circuit, which will be more fully explained later. Such constituted water content sensing unit, represented by the reference numeral 8, is inserted into a commonly used cloth type or paper type diaper 9 as shown in FIG. 3. The metal layers 2 and 3 and the electric insulating layer 4 covered on the layer 2 will function as a capacitor when the water is present between the two metal layers 2 and 3. The electrostatic capacitance of this capacitor is varied in accordance with the amount of the absorbed water.

Figure 4:
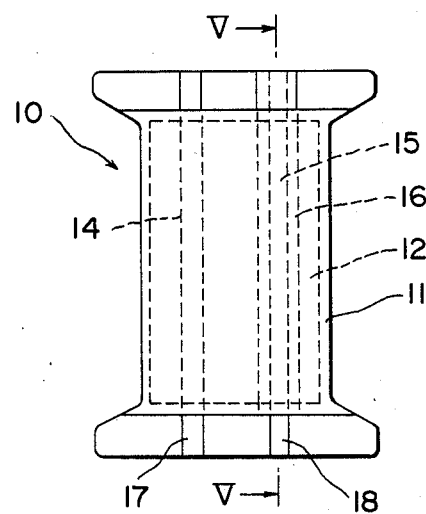
FIG. 4 is a plan view showing a disposable diaper with another embodiment of the sensing unit of the water content detecting device according to the present invention.
Figure 5:
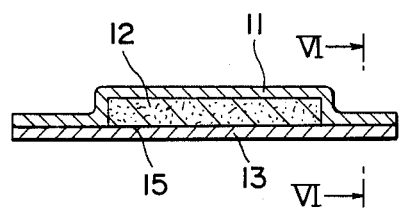
FIG. 5 is a sectional view taken along the line V—V of FIG. 4.
Figure 6:
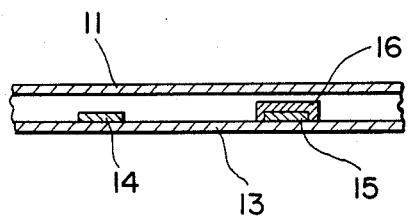
FIG. 6 is a sectional view taken along the line VI—VI of FIG. 5.

FIG. 4 is a plan view showing another embodiment of the water content sensing unit which is previously assembled within a disposable diaper 10. FIG. 5 is a sectional view taken along the line V—V of FIG. 4. FIG. 6 is also a sectional view and is taken along the line VI—VI of FIG. 5. The disposable diaper 10 is composed of a water permeable inner sheet 11, a water absorber 12 and a water impermeable outer sheet 13. The water permeable inner sheet 11 is a non-woven sheet with a texture rate of 10 to 30 g/m$^2$ such as rayon, polypropylene or polyester fiber, or porous and deposing treated plastic film having its thickness of 50 $\mu$m or less. The water absorber 12 is a structural material made of cotton pulp, tissue paper, super absorbing polymer, or the like. The outer sheet 13 is plastic film having its thickness of 30 $\mu$m or less and made of polyethylene, polypropylene, polyester or the like. Further, as shown in FIGS. 5 and 6, a pair of metal layers 14 and 15 are formed on the outer sheet 13 in the same manner as the metal layers 2 and 3 of the water content sensing unit 8 before memtioned, so that they are placed between the outer sheet 13 and the water absorber 12. This pair of metal layers are separated with constant distance and extend in parallel to each other in the longitudinal direction of the diaper 10. One surface of either one of metal layers 14 and 15 in this embodiment, the metal layer 15, can be covered with an electric insulating layer 16 as shown in FIG. 6. The metal layers 14 and 15 are connected to leads 17 and 18 formed on one end of the outer sheet 13. The leads 17 and 18 are further connected to a water content detecting circuit, referred later in detail.

In this diaper 10, the metal layers 14 and 15 and the electric insulating layer 16 will function as a capacitor. The electrostatic capacitance of this capacitor is also varied in accordance with the amount of water absorbed in the water absorber 12.

Figure 7:
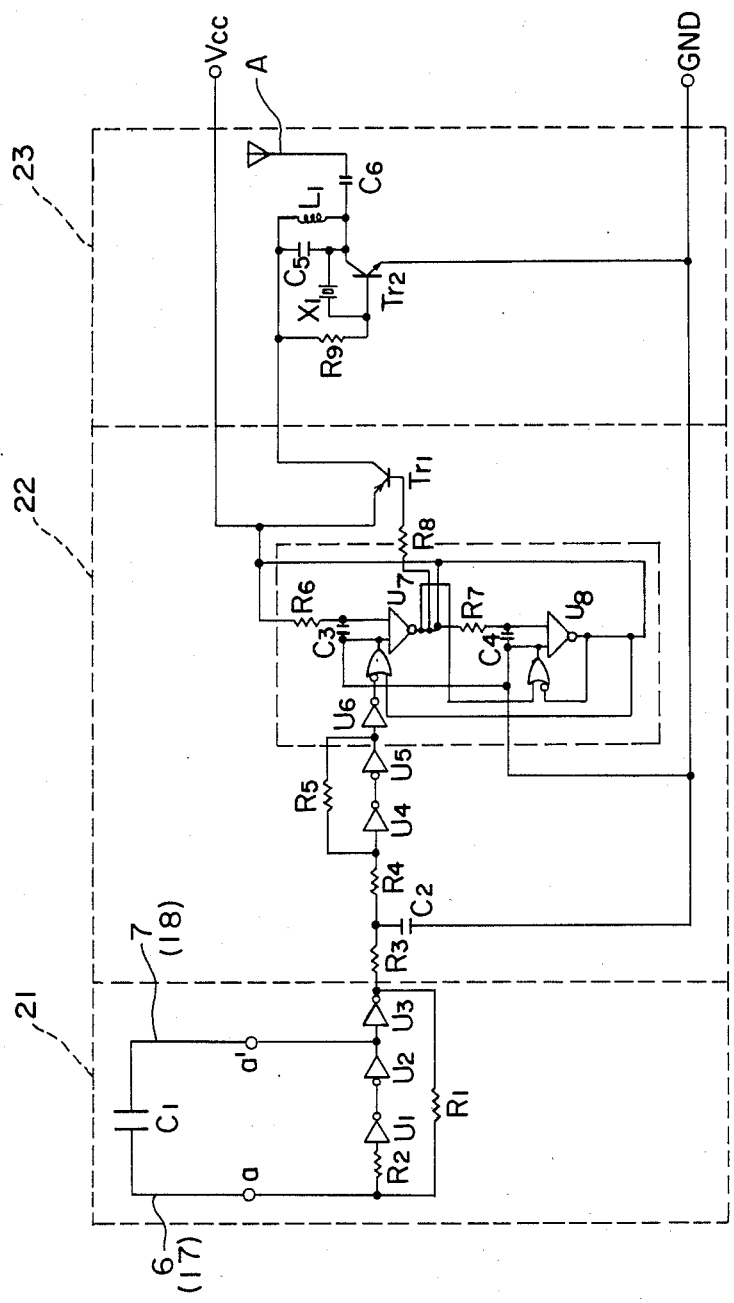
FIG. 7 is a circuit diagram showing an embodiment of an informing unit of the water content detecting device according to the present invention.

Referring to FIG. 7, there is shown a circuit diagram of an informing unit containing a water content detecting circuit 21, a wave form shaping circuit 22 and a high frequencey oscillating circuit 23. The water content detecting circuit 21 mainly consists of an astable multivibrator which comprises a capacitor C1 corresponding to the water content sensing unit 8 before mentioned, terminals a and a' which are respectively connected to the leads 6(17) and 7(18) from the capacitor C1, a feedback resistor R1, a current limiting resistor R2, and inverters U1, U2, and U3. The capacitor C1 is also a feedback capacitor for this circuit. The inverters U1, U2, and U3 are composed of digital IC. The output side of the inverter U2 is connected to the capacitor C1.

The value of the feedback resistor R1 is so determined that the inverters U1, U2, and U3 start oscillation whenever the electrostatic capacitance of the capacitor C1 reaches a predetermined value. Thus the inverter U3 generates a pulse signal and feeds this signal to the wave form shaping circuit 22.

The wave form shaping circuit 22 mainly comprises a shaping circuit consisting of resistors R3 and R4 and a capacitor C2. Further, a series of inverters U4, U5, and U6 and a monostable multivibrator are succeedingly connected. This monostable multivibrator comprises capacitors C3 and C4, resistors R6 and R8 and inverters U7 and U8. The values of these capacitors C3 and C4, and resistors R6 and R7 are so determined as to generate a shaped pulse output having a suitable frequency. The pulse output is applied to the base of a transistor Tr1 through a resistor R8.

The oscillating circuit 23 comprises a transistor Tr2 the base of which is connected to the transistor Tr1 through a resistor R9, a crystal resonator X1, capacitors C5 and C6, an inductance L1, and an antenna A. The actuating voltage is applied to the base of the transistor Tr2 from a power source Vcc through the resistor R9 when the transistor Tr1 is turned on. The transistor Tr2 is also turned on. Then the crystal resonator X1 is energized, so that the crystal resonator X1 outputs an oscillating signal. This signal is oscillatingly output from the antenna A by the resonance effect of the capacitor C5 and the inductance L1. The oscillation signal is received by a receiver, not shown, at a remote place such as a nurses center. This received signal is amplified and output as an information by means of a visual or audio device.

In this embodiment, the value of the feedback resistor R1 in the water content detecting circuit 21 is set in a range of 5 to 100K $\Omega$; and the electrostatic capacitance of the capacitor C1 formed in the sensing unit 8 or the disposable diaper 20 is set in a range of 5000 to 500 PF. When the degree of wetness of the diaper is low, the electrostatic capacitance of the capacitor C1 can not reach to the set range. This case can not actuate the multivibrator of the water content detecting circuit 21. On the other hand, as the degree of wetness of the diaper reaches to the specific level that the patient may feel unpleasant, the electrostatic capacitance of the capacitor C1 coincides with the set range. The input terminal of the inverter U1 is alternatingly applied with a high level and low level signals, so that the multivibrator starts its oscillating operation and outputs an oscillating pulse signal to the wave form shaping circuit 22. Then the circuit 22 outputs a shaped pulse signal having a predetermined frequency and then the high frequency oscillating circuit 23 generates the oscillating signal to inform that the diaper should be changed to a nursing person at a remote place.

It should be appreciated while the various embodiments of the present invention have been described in specific detail, numerous additions, omissions and modifications are possible within the intended spirit and scope of the invention.

What is claimed is:

1. A water content detecting device for any type of diaper, comprising:
    a sensing unit for sensing the degree of wetness in a diaper, said sensing unit including a water permeable upper sheet, a water impermeable lower sheet and pair of metal layers positioned intermediate said water permeable upper sheet and said water impermeable lower sheet, one of said pair of metal layers being covered with an electrical insulating layer;
    a water content detecting circuit for detecting a change in electrostatic capacitance between said pair of metal layers of said sensing unit, said water content detecting circuit including a multivibrator, said pair of metal layers of said sensing unit, said water content detecting circuit including a multivibrator, said pair of metal layers of said sensing unit forming a feedback capacitor of said multivibrator;
    a wave form shaping circuit operably associated with said water content detecting circuit; and
    an oscillating circuit operably associated with said wave form shaping circuit for transmitting a signal indicating that the diaper is wet.

2. The device of claim 1, wherein:
    said sensing unit is detachably connected to the diaper.

3. The device of claim 2, wherein:
    said diaper is formed from cloth.

4. the device of claim 2, wherein:
    said diaper is formed from paper.

5. The device of claim 1 wherein:
    said multivibrator of said water detecting circuit includes first and second terminals operably associated with said pair of metal layers, a feedback resistor, a current limiting resistor, and first, second, and third inverters;
    said first, second and third inverters are connected in series;
    said first, second and third inverters each have an input and output side; and
    said output side of said second inverter is connected to said feedback capacitor.

* * * * *